United States Patent [19]

Nelson

[11] Patent Number: 5,714,887
[45] Date of Patent: Feb. 3, 1998

[54] FIXTURE FOR USE IN MICROWAVE GRAIN MOISTURE MEASUREMENT

[75] Inventor: George F. Nelson, Coon Rapids, Minn.

[73] Assignee: New Holland North America, Inc., New Holland, Pa.

[21] Appl. No.: 644,185

[22] Filed: May 10, 1996

[51] Int. Cl.$^6$ ................................................ G01N 22/04
[52] U.S. Cl. ................................ 324/640; 73/73
[58] Field of Search ................................ 324/637, 639, 324/640; 73/73

[56] References Cited

U.S. PATENT DOCUMENTS

| | | | |
|---|---|---|---|
| 3,360,721 | 12/1967 | Pullman | 324/640 |
| 4,066,951 | 1/1978 | Wang | 324/689 |
| 4,716,360 | 12/1987 | Pakulis | 324/640 |

*Primary Examiner*—Glenn W. Brown
*Attorney, Agent, or Firm*—Griffin, Butler, Whisenhunt & Kurtossy

[57] ABSTRACT

A fixture for use in the microwave measurement of the moisture content of grain comprises a hollow support member, an antenna support assembly supporting antennas for transmitting and receiving microwaves, and a sample scoop. The support member, antenna support assembly and scoop are made of a low dielectric plastic material which has negligible effect on the microwaves. The antenna support assembly includes a cylindrical sleeve with two support stubs extending radially outwardly from the sleeve. The support member has two recesses in its top surface for receiving the stubs so as to position the antenna support assembly and the antennas relative to the support member. The sleeve has an inside diameter slightly greater than the outside diameter of the scoop so that the scoop may be inserted into the sleeve and rest on the same supporting surface as the support member. The arrangement is such that when the scoop is loaded with a sample of grain and inserted through the sleeve, the center of the grain sample is substantially aligned with the antennas.

14 Claims, 3 Drawing Sheets

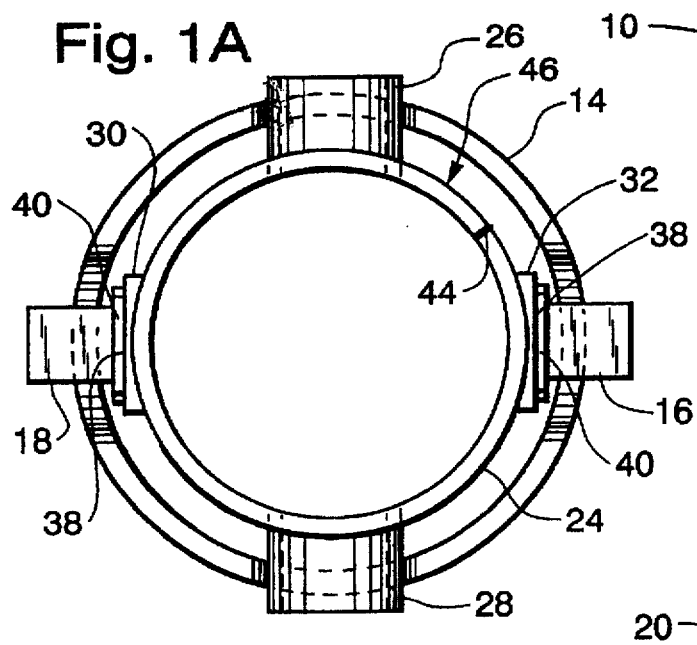
Fig. 1A
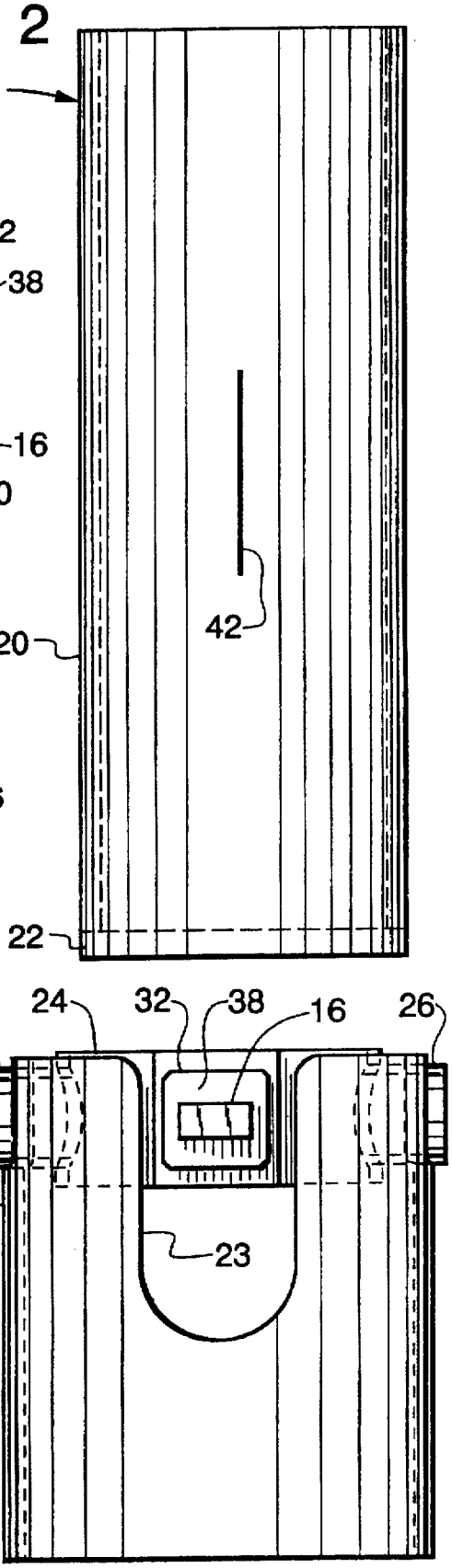
Fig. 2
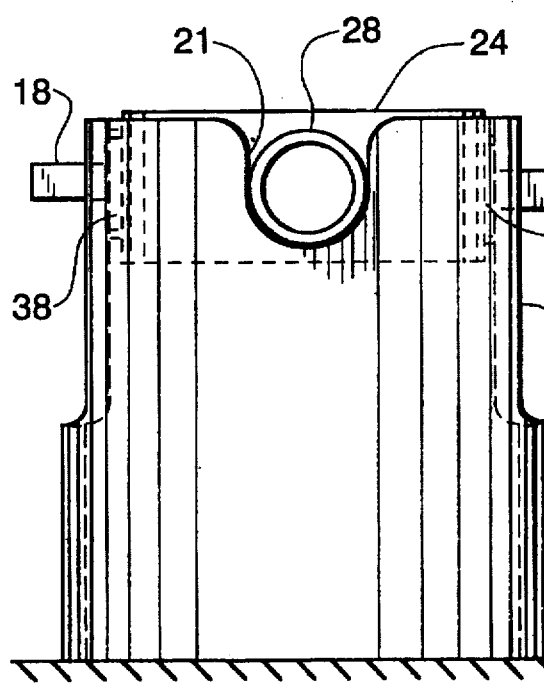
Fig. 1B
Fig. 1C

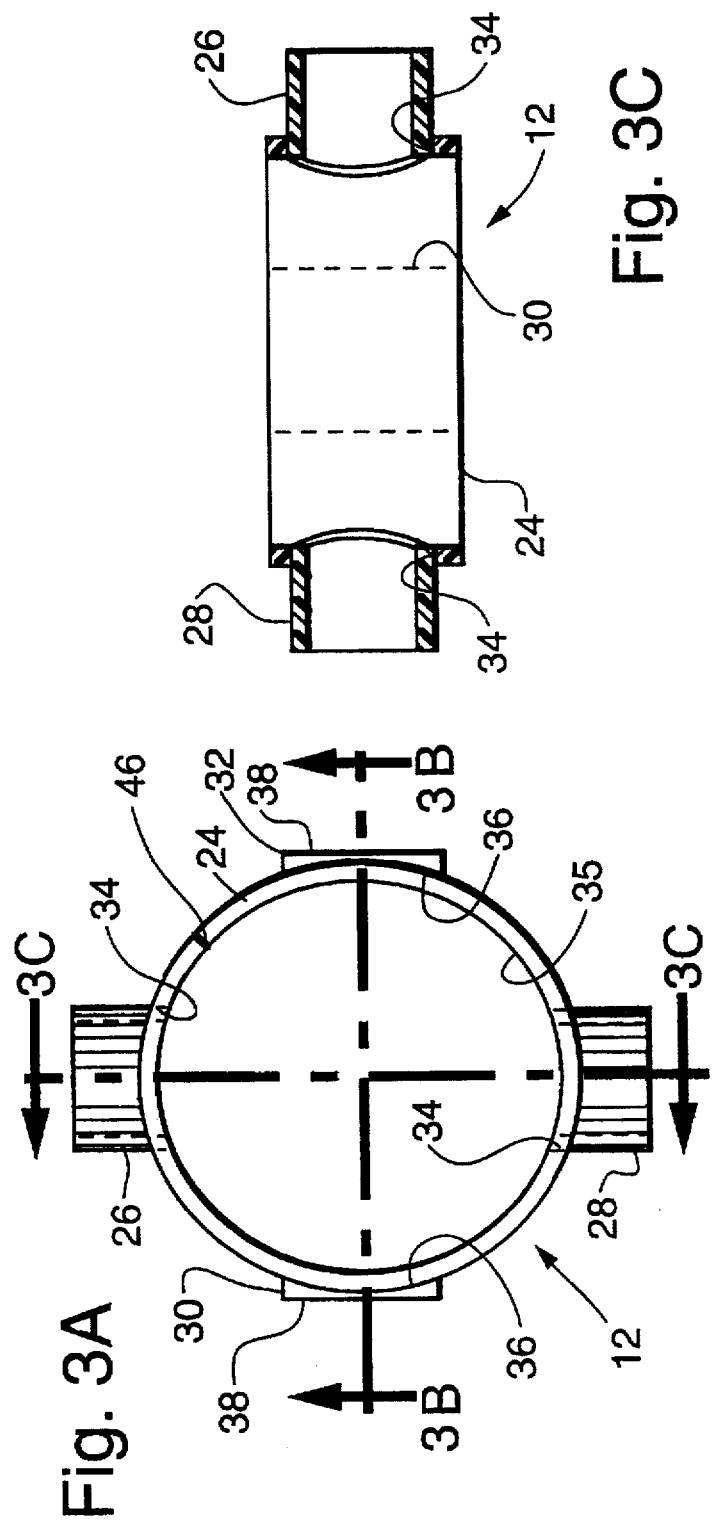

5,714,887

1

FIXTURE FOR USE IN MICROWAVE GRAIN MOISTURE MEASUREMENT

FIELD OF THE INVENTION

The present invention relates to apparatus for use in carrying out measurements of the moisture content of grain. More specifically, the invention relates to a fixture particularly suitable for carrying out measurements of grain moisture content on batch samples in a laboratory, at a grain elevator, or even on a farm.

BACKGROUND OF THE INVENTION

It is customary to base the sale price of grain on its quality and moisture content. Since the price is determined in part by the moisture content it is imperative to use the most accurate means available to determine the moisture content.

Various methods are currently used in making the moisture content measurement, the particular method employed depending on the desired accuracy and the speed of the measurement. One method, which is the most accurate and has been accepted by the ASAE, is the oven-dry method. In this method the grain is sampled, the sample is weighed, and then placed in an oven at a prescribed temperature for a specific period of time depending on the type of grain. After the sample has been in the oven for the specified period of time, it is removed from the oven and again weighed. The difference in weight for a fixed quantity of grain provides an indication of the moisture content.

A second method utilizes the capacitance effect of the moist grain between two low frequency RF electrodes. The accuracy of this method is on the order of a few percent moisture content as compared to an accuracy of 0.1–0.25 percent for the oven-dry method. The reason is that the second method measures the ionic conductivity of the grain and the surface moisture of the grain dominates over the internal grain moisture. Furthermore, in the capacitance method it requires hours for the moisture in wetted grain to equilibrate so that the measurement produces a result even close to the kernel moisture content.

More recently, microwave RF on the order of a few to many gigahertz has been used to determine grain moisture content. This method has an accuracy comparable to the oven-dry method because at frequencies in the gigahertz range the effects of ionic conductivity are eliminated or greatly reduced. In addition, measurements of moisture content using the microwave method may be accomplished in considerably less time compared to either the oven-dry or capacitance method. The actual measurement requires only a few milli-seconds once the sample is in position for the measurement.

The microwave measurement of grain moisture content is carried out by transmitting a 1–10 GHz microwave test signal through a grain sample and measuring the effect of the grain on the phase shift and attenuation of the signal. The phase/attenuation ratio for a specific grain type is compared to a calibration comprised of previous laboratory measurements. The laboratory measurements provide a calibration regression equation for phase/attenuation ratio value to moisture content. The measured grain ratio is compared to this calibration equation and a moisture content prediction for the grain under test is produced.

A need exists for a laboratory or bench-type fixture which will facilitate the taking of grain samples and the proper positioning of the samples relative to the antennas of a microwave RF grain moisture measurement apparatus so that the microwave measurement method may be quickly carried out by operators having no particular skill.

SUMMARY OF THE INVENTION

An object of the present invention is to provide a fixture for use in the microwave RF measurement of the moisture content of grain, the fixture comprising only materials which are transparent to, or have negligible effect on the microwave test signal.

Another object of the invention is to provide a fixture for use in microwave RF measurement of grain moisture content, the fixture enabling an operator of no particular skill to take a grain sample from a grain supply and accurately position the sample relative to the antenna means of the measurement apparatus.

The fixture comprises a scoop for scooping up a test sample of grain, an antenna support assembly having a sleeve for slidably receiving the scoop, a transmit antenna and a receive antenna mounted on the sleeve at diametrically opposed locations so that a microwave test signal transmitted by the transmit antenna passes through the grain sample to the receive antenna, and a support member for supporting the antenna support assembly so that the antennas are positioned at approximately the mid-point of the grain sample in the axial direction. The scoop, sleeve and support member are all hollow cylindrical members made of a low dielectric plastic material, such as polyvinylchloride which has little or no effect on the microwave test signal.

Other objects and advantages of the invention and the manner of making and using it will become obvious upon consideration of the following description and the accompanying drawings.

BRIEF DESCRIPTION OF THE DRAWINGS

FIGS. 1A, 1B and 1C are top, front elevation and side elevation views, respectively, of an apparatus for measuring the moisture content of a batch of grain, FIG. 1B showing the fixture resting on a supporting surface;

FIG. 2 is an elevation view of a sample scoop used with the apparatus of FIGS. 1A–1C;

FIG. 3A is a top view of an antenna support assembly;

FIG. 3B is a sectional view of the antenna support assembly taken along the line B—B of FIG. 3A;

FIG. 3C is a sectional view of the antenna support assembly taken along the line C—C of FIG. 3A;

DETAILED DESCRIPTION OF THE INVENTION

Figure 5:
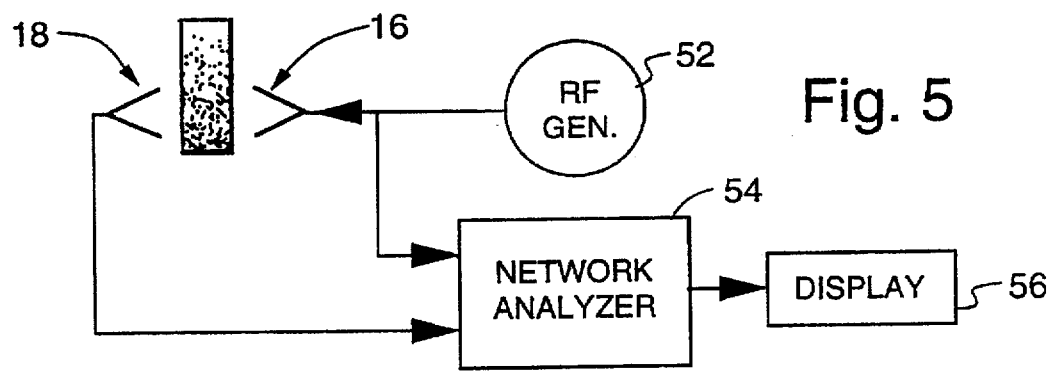

In accordance with the present invention a fixture for use in measuring the moisture content of grain comprises a sample holder or scoop 10 (FIG. 2) for holding a batch sample of grain, an antenna support assembly 12 (FIGS. 3A–3C), a support member 14 (FIGS. 4A–4C) for supporting the antenna support assembly 12, and microwave antenna means including a transmit antenna 16 (FIG. 1A) and a receive antenna 18.

The scoop 10 comprises a hollow cylindrical body 20 which is closed at its bottom by a circular sheet or plate 22. The plate is preferably glued to the bottom surface of body 20. Although not shown in the drawing, scoop 10 may be provided with a plastic strap or other handle attached to the upper portion of body 20 to facilitate handling of the scoop.

Scoop 10, antenna support assembly 12 and sleeve support 14 are made of a low dielectric plastic material such as polyvinylchloride (PVC) or a similar material which is transparent to, and has minimal effect on, microwaves in the 1–10 GHz frequency range.

Figure 4A:
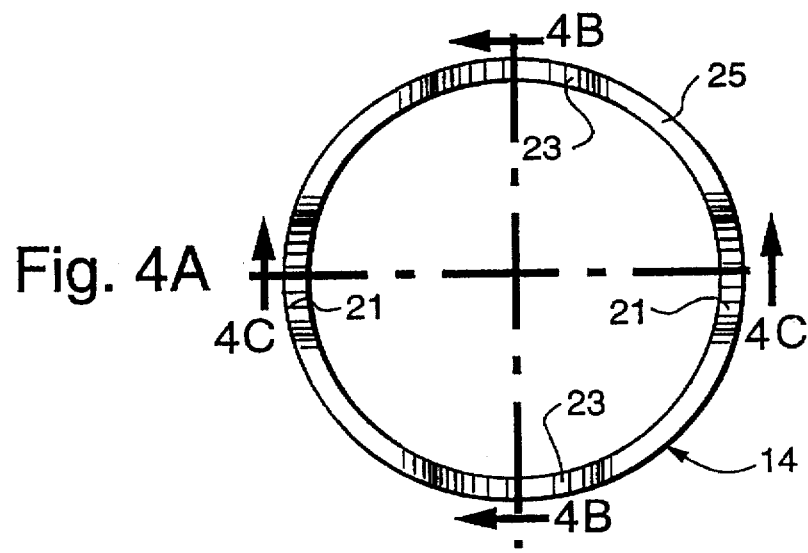
FIG. 4A is a top view of a support member for supporting the antenna support assembly.
Figures 4B, 4C:
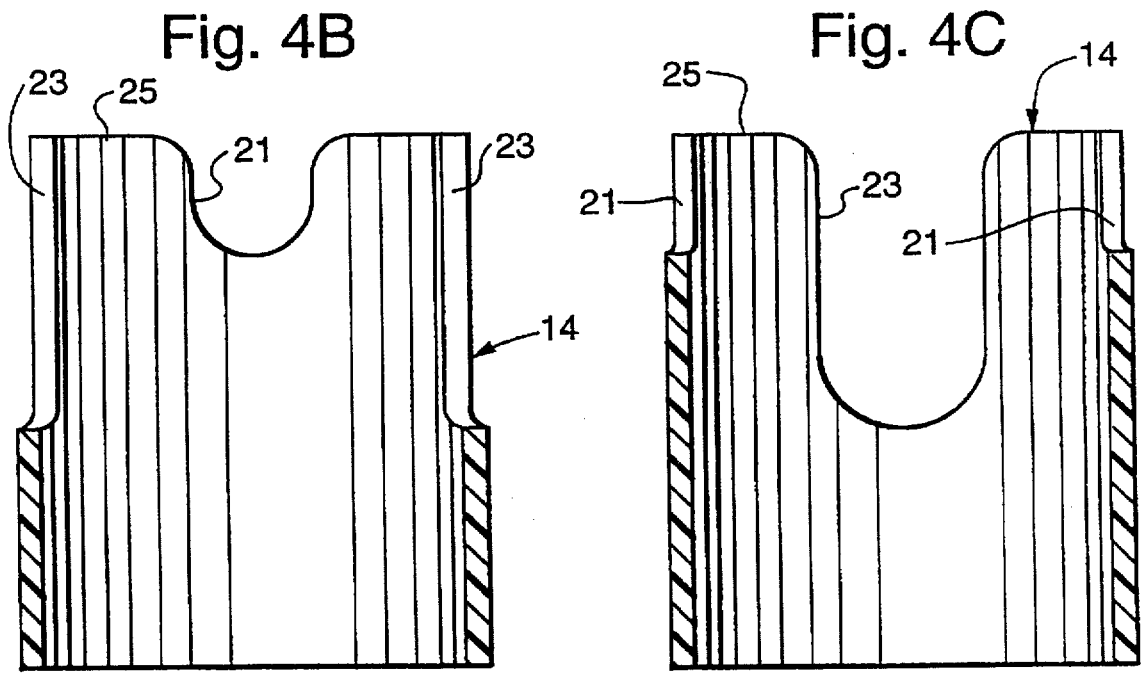
FIG. 4B is a sectional view of the support member taken along the line B—B of FIG. 4A.
FIG. 4C is a sectional view of the support member taken along the line C—C of FIG. 4A; and, FIG. 5 illustrates a grain moisture content measurement system in which the fixture may be utilized.

As shown in FIGS. 4A–4C, the support member 14 comprises a hollow cylindrical body having first and second diametrically opposed recesses 21 and third and fourth diametrically opposed recesses 23 all extending axially into the body from its top surface 25. As subsequently explained, recesses 21 receive two cylindrical support stubs 26, 28 provided on antenna support assembly 12 and the bottoms of these recesses are semi-circular to support and position the stubs. Recesses 23 provide clearance for the antennas 16 and 18 because the antenna support assembly 12 supports the antennas at a level below the top surface 25 of the support member 14 when stubs 26, 28 are positioned in the recesses 21. The support member may be 6" diameter Schedule 40 PVC pipe to provide stability. The bottom of support member 14 is normally open and is closed by a flat surface 50 (FIG. 1B) of a table or work bench on which the fixture rests while measurements are being made. If desired, a flat sheet of PVC may be glued to the bottom of the support member to further reduce the possibility of tipping over.

As shown in FIGS. 3A–3C, the antenna support assembly 12 includes a hollow cylindrical sleeve 24, first and second support stubs or arms 26, 28, and first and second mounting blocks 30, 32. The internal diameter of sleeve 24 is slightly greater than the outside diameter of scoop 10 so that the scoop is insertable into the sleeve from the top and slidable through the sleeve until the bottom of the scoop rests on the flat surface 50 or, if support element 14 is provided with a bottom closure, until the bottom of the scoop rests on the bottom closure for the support element. In a working embodiment, the sleeve 24 comprises a machined-out PVC end cap for a 4" PVC pipe and has an internal diameter of 4.62". The scoop 10 comprises a piece of 4" diameter Schedule 40 PVC pipe (O.D. 4.52").

Sleeve 24 is provided with two diametrically opposed circular openings 34 for receiving one end of a respective one of the stubs 26, 28. The stubs may be pieces of 1¼" Schedule 40 PVC pipe. The ends of the studs are shaped to have a curvature corresponding to the internal surface 35 of sleeve 24 so that the ends of the stubs lie flush with the internal surface of the sleeve. The stubs 26, 28 are glued in place and extend radially outwardly from the sleeve 24 in opposite directions.

The first and second mounting blocks 30, 32 are glued to the outside surface of sleeve 24. The surfaces 36 of the mounting blocks facing sleeve 24 are shaped to match the curvature of the outside surface of the sleeve. The mounting block surfaces 38 are flat so as to be parallel to each other when the mounting blocks are mounted at diametrically opposed positions on sleeve 24. Preferably, the mounting blocks 30, 32 are angularly displaced 90° relative to the stubs 26, 28.

The antenna support assembly 12 is mounted on support member 14 with support stubs 26, 28 resting in the bottoms of recesses 21, 23 and sleeve 24 coaxially positioned relative to the support member. The antenna support assembly may be attached to the support member with fasteners, or by glue placed in the regions where support stubs 26, 28 rest on the support member.

The antennas 16, 18 are horn type microwave antennas of conventional design. In a working test model of the invention, WR90 waveguide to coax adapters (Loral Microwave-Narda Model 4601) were used as antennas. However, it is anticipated that printed circuit board patch gain antennas will be suitable for use in production models.

Each antenna includes an integral mounting flange 40 (FIGS. 1A and 1C) and each mounting flange 40 is attached by glue or screws to the flat surface 38 of one of the mounting blocks 30, 32. Because surfaces 38 are parallel, this positions the antennas so that microwaves transmitted from the horn of antenna 16 are directed toward the horn of receiving antenna 18.

It will be understood that each antenna 16, 18 is provided with a connector (not shown) so that the transmit antenna 16 may be energized from an RF source 52 (FIG. 5), preferably at a frequency of about 10 GHz, and signals received by the receive antenna 18 may be fed to a conventional analyzing circuit 54 (a Hewlett-Packard HP8510 network analyzer, for example) which determines the effect of grain moisture content on the amplitude and phase of the signal transmitted through the sample, and displays the results on display 56.

To use the fixture in the measurement of the moisture content of grain, the support member 14 is placed on a flat horizontal surface. The source of RF signals is connected to the transmit antenna 16 and the output of the receive antenna 18 is connected to the signal analyzer. The RF source and output signal analyzer are then energized. At this time the support member 14 and antenna support assembly 12 are as shown in FIGS. 1A–1C and measurements may now be made.

For each measurement, the scoop 10 is filled by dipping it into a supply of grain whose moisture content is to be measured. The amount of grain collected in the scoop is not critical as long as it exceeds a minimum quantity. In this regard, in a working model of the invention, the support member 14 measures 8" in the axial or vertical direction, the scoop 10 measures 13.55" from the top of circular plate 22 to the top of circular body 20, and the antenna support assembly 12 supports the antennas so that the centers of the horns are 6.57" above the bottom of support member 14. Given a fixture of these dimensions, scoop 10 should filled to a level which is within at least 1½" of its top to thereby insure that the grain sample extends above the horns at least as far as it extends below the horns.

After scoop 10 has been filled with a batch of grain, the scoop is inserted through the sleeve 24 until the bottom of the scoop rests on the same surface as the support member 14 (or on the bottom closure of support member 14 if it is provided with one). The microwave signal produced by antenna 16 passes through the grain where the signal is shifted in phase and changed (attenuated) in magnitude before it reaches the antenna 18. The resulting output signal from antenna 18 is analyzed to determine the phase shift and attenuation of the signal transmitted from antenna 16. The analysis requires only a few milli-seconds. The scoop 10 may then be removed from sleeve 24, the grain emptied therefrom, and the scoop filled with a new sample of grain in preparation for a new measurement of grain moisture content.

As shown in FIG. 2, the scoop 10 is provided with a first fiducial marking 42 extending axially along the outer surface of cylindrical body 20. A second fiducial marking 44 is provided on the top surface 46 of sleeve 24. Each time the scoop. is inserted into sleeve 24 to make a measurement of moisture content, the first and second fiducial markings should be aligned. In the event that scoop 10 contains defects or anomalies which affect the microwave signal, alignment of the first and second fiducial markings insures that the defects or anomalies affect all measurements to exactly the same degree.

From the foregoing description it is seen that the present invention provides a simple and easy to use fixture for the measurement of grain moisture content. The fixture is inexpensive to make, its major components being PVC pipe or sheets of PVC. It is made of non-conductive materials hence the fixture has minimal adverse influence on the accuracy of measurements. The quantity of grain in samples is not critical and the taking of samples and the placing of samples into the fixture is quickly accomplished even by operators having no particular skill. The measuring apparatus operates continuously so that an operator does not have to initiate each measurement but only has to insert and remove samples from the fixture. Finally, the grain samples may be relatively small thereby limiting incorrect measurements due to any moisture gradient over a total sample.

While a preferred embodiment has been described in detail to illustrate the principles of the invention, various modifications and substitutions may be made in the described embodiment without departing from the spirit and scope of the invention as defined in the appended claims. For example, the scoop 10, support members 14 and sleeve 24 need not be cylindrical but may, for example, have a rectangular cross-section. Elements of non-circular cross-section would increase the cost of the fixture and greater care would have to be exercised in positioning the scoop relative to the sleeve and antennas.

As a further modification, the transmit/receive means may comprise a transmit/receive antenna mounted on only one of the mounting blocks 30, 32 so that the measurement signal is obtained by reflection of the transmitted signal from the grain sample. It has been found that for a given grain sample the magnitude of the reflected signal is greater than the magnitude of a signal which passes through the grain sample from a transmitting antenna to a receiving antenna arranged as shown in FIG. 1A.

I claim:

1. A fixture for use in the measurement of the moisture content of grain, said fixture comprising:
    a sample scoop comprising a hollow body, closed at one end, for holding a test grain sample;
    an antenna support assembly comprising a sleeve and first and second support stubs extending outwardly from said sleeve,
    said sleeve having internal dimensions slightly greater than outside dimensions of said scoop so that said scoop is slidably receivable into said sleeve;
    antenna means mounted on said sleeve; and,
    a hollow support member for supporting said antenna support assembly, said support member having first and second recesses extending axially into said support member from a top surface of said support member, said recesses being shaped to receive said first and second support stubs, respectively, to thereby position and support said antenna support assembly relative to said support member.

2. A fixture as claimed in claim 1 wherein said sample scoop, said antenna support assembly and said support member all comprise a low dielectric material.

3. A fixture as claimed in claim 1 wherein said sample scoop, said antenna support assembly and said support member all consist of polyvinylchloride.

4. A fixture as claimed in claim 1 wherein said sample scoop, said sleeve and said support member are circular in shape, said support member having an internal diameter and said sleeve having an external diameter less than the internal diameter of said support member whereby said sleeve is supported within said support member when said first and second support stubs rest in said first and second recesses.

5. A fixture as claimed in claim 1 wherein said antenna means comprises a microwave transmit antenna and a microwave receive antenna mounted on an outer surface of said sleeve and facing each other whereby microwaves transmitted by said transmit antenna pass through a grain sample and are received by said receive antenna when said scoop is received into said sleeve.

6. A fixture as claimed in claim 5 wherein said support member includes third and fourth recesses extending axially into said support member from said end surface for receiving said transmit antenna and said receive antenna as said first and second support stubs are received into said first and second recesses.

7. A fixture for use in the measurement of the moisture content of grain, said fixture comprising:
    a sample scoop for holding a test grain sample, said scoop comprising a cylindrical body closed at one end;
    an antenna support assembly comprising a cylindrical sleeve and first and second diametrically opposed support stubs extending radially outwardly from said sleeve;
    a transmit antenna for transmitting microwaves and a receive antenna for receiving microwaves transmitted by said transmit antenna, said transmit antenna and said receive antenna being mounted on said sleeve at diametrically opposed positions; and,
    a hollow cylindrical support member for supporting said transmit antenna and said receive antenna at a fixed axial distance from a bottom surface of said hollow cylindrical member, said hollow cylindrical support member having first and second diametrically opposed recesses extending into said support member from a top surface of said support member, said first and second recesses being shaped to receive and engage said first and second support stubs, respectively,
    said sleeve having an internal diameter and said scoop having an external diameter slightly less than the internal diameter of said sleeve whereby said scoop is insertable into, and slidable relative to said sleeve,
    said support member having an internal diameter and said sleeve having an external diameter less than the internal diameter of said support member whereby said sleeve is supported within said support member.

8. A fixture as claimed in claim 7 wherein said support member, said scoop and said first and second support stubs comprise lengths of polyvinylchloride pipe.

9. A fixture as claimed in claim 7 wherein said scoop, said antenna support assembly and said support member comprise a low dielectric plastic material having minimal effect on microwaves transmitted by said transmit antenna.

10. A fixture as claimed in claim 7 wherein said transmit antenna transmits microwaves having a frequency of about 10 GHz.

11. A fixture as claimed in claim 7 wherein said support member has an open bottom adapted to be closed by a flat surface on which said support member is disposed, said scoop being slidable through said sleeve until the closed end of the scoop rests on said flat surface.

12. A fixture as claimed in claim 11 wherein said scoop has an axial length at least twice as great as said fixed axial distance.

13. A fixture as claimed in claim 7 wherein said sleeve is provided with two openings one end of each of said first and second support stubs being glued into a respective one of said openings.

14. A fixture as claimed in claim 7 wherein said scoop and said sleeve are provided with fiducial markings for angularly orienting said scoop relative to said sleeve whereby said scoop always affects microwaves emitted by said transmit antenna to the same degree each time said scoop is inserted into said sleeve with said fiducial markings in alignment.

* * * * *